(12) United States Patent
Denu et al.

(10) Patent No.: US 8,440,638 B2
(45) Date of Patent: May 14, 2013

(54) COMPOSITIONS AND METHODS FOR MODULATING CALCIUM FLUX, GLUCOSE HOMEOSTASIS AND APOPTOSIS

(75) Inventors: John M. Denu, McFarland, WI (US); Andrew M. Scharenberg, Seattle, WA (US)

(73) Assignees: Wisconsin Alumni Research Foundation, Madison, WI (US); University of Washington, Seattle, WA (US)

( * ) Notice: Subject to any disclaimer, the term of this patent is extended or adjusted under 35 U.S.C. 154(b) by 1386 days.

(21) Appl. No.: 11/658,069

(22) PCT Filed: Jul. 20, 2005

(86) PCT No.: PCT/US2005/025625
§ 371 (c)(1),
(2), (4) Date: May 28, 2008

(87) PCT Pub. No.: WO2006/068668
PCT Pub. Date: Jun. 29, 2006

(65) Prior Publication Data
US 2008/0249059 A1  Oct. 9, 2008

Related U.S. Application Data

(60) Provisional application No. 60/589,269, filed on Jul. 20, 2004.

(51) Int. Cl.
*A61K 31/7076* (2006.01)
*A61K 31/7052* (2006.01)
*A61K 31/455* (2006.01)
*C07H 19/167* (2006.01)
*C07H 19/20* (2006.01)
*C07H 19/173* (2006.01)

(52) U.S. Cl.
USPC ............ 514/45; 514/46; 514/47; 514/42; 514/356; 536/22.1; 536/27.6; 435/375

(58) Field of Classification Search ............ 514/45, 514/46, 47, 42, 356; 536/22.1, 27.6; 435/375
See application file for complete search history.

(56) References Cited

PUBLICATIONS

Ise et al. (Hyogo Ika Daigaku Igakkai Zasshi (1977), 2(3), 237-42) (Abstract sent).*
Antione et al. (Diabetologia (2004) 47:909-916).*
O'Brien et al. (The Journal of Pathology, (May 2000) vol. 191, No. 1, pp. 86-92).*
Soderlund et al. (Neoplasma vol. 51, p. 1-11, 2004) (Abstract sent).*
Lebovitz, et al. (Endocrinology (1967), 80(4), 656-62) (Abstract sent).*
Hardikar et al. (Endocrinology, Sep. 2002, 143(9):3505-3514).*
Antoine, M., et al. "Tricyclic antidepressant imipramine reduces the insulin secretory rate in islet cells of Wistar albino rats through a calcium antagonistic action" Accession No. 2004: 455165 CAPLUS; Document No. 142: 32791; Diabetologia (2004) 47(5) 909-916.
O'Brien, B.A. et al. "Nicotinamide prevents the development of diabetes in the cyclophosphamide-induced NOD mouse model by reducing beta-cell apoptosis" Accession No. 200231982 Medline; Document No. PubMED ID: 10767724; The Journal of Pathology May (2000) vol. 191 (1) 86-92.
Moazed, D. "Enzymatic activities of Sir2 and chromatin silencing" Current Opinion in Cell Biology (2001) 13: 232-238.
Jackson, Michael D. et al. "Structural identification of 2' - and 3'O-Acetyl-ADP-ribose as novel metabolites derived from the Sir2 family of β-NAD+-dependent histone/protein deacetylases" vol. 277 No. 21 (May 24, 2002) 18535-18544.

* cited by examiner

*Primary Examiner* — Shaojia Anna Jiang
*Assistant Examiner* — Michael C Henry
(74) *Attorney, Agent, or Firm* — Dann Dorfman Herrell & Skillman; Robert C. Netter, Jr.

(57) ABSTRACT

Compositions and methods are disclosed which are effective for modulating glucose homeostasis, calcium ion flux and cell death in target cells.

3 Claims, 5 Drawing Sheets

Fig 3
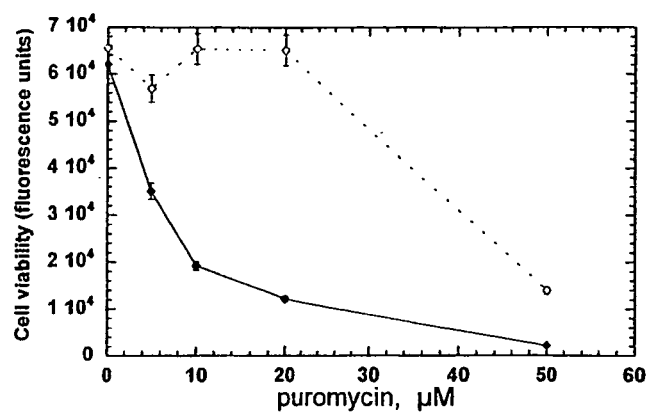
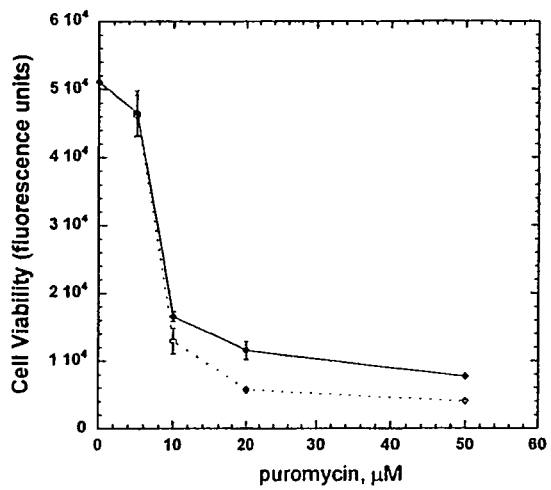

Fig 4
a
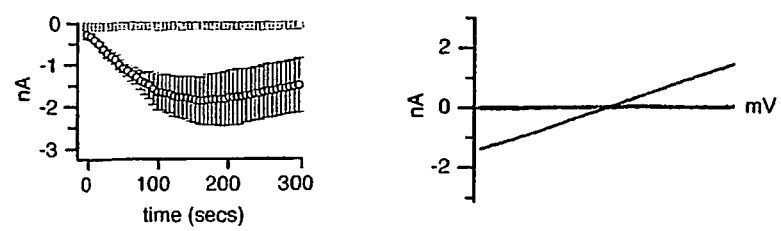
b
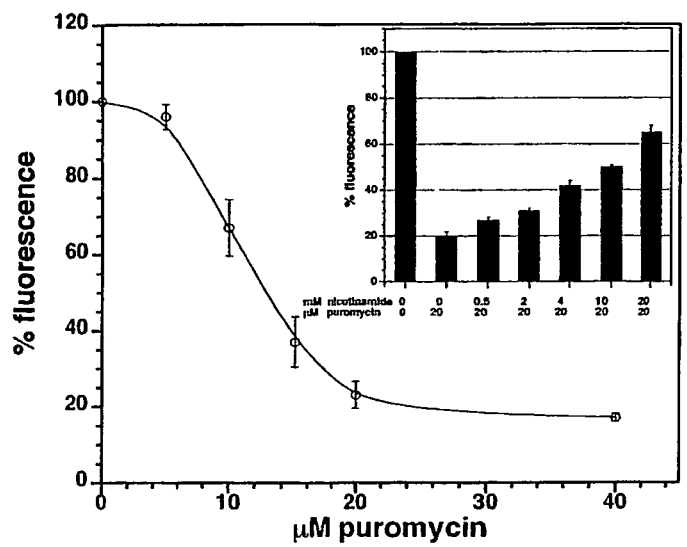

US 8,440,638 B2

COMPOSITIONS AND METHODS FOR MODULATING CALCIUM FLUX, GLUCOSE HOMEOSTASIS AND APOPTOSIS

This application is a §371 application of PCT/US2005/025625, filed Jul. 20, 2005, which claims priority to U.S. Provisional Application 60/589,269 filed Jul. 20, 2004. The entire disclosure of each of the above identified applications is incorporated herein by reference.

Pursuant to 35 U.S.C. §202(c), it is acknowledged that the U.S. Government has certain rights in the invention described herein, which was made in part with funds from the National Institutes of Health, Grant Number GM65386 and GM64091.

FIELD OF THE INVENTION

This invention relates to the fields of biochemistry, aging, diabetes and oncology. More specifically, the present invention provides compositions and methods for modulating cell death (e.g., apoptosis) in target cells, particularly cancer cells. The invention also provides compositions and methods for modulating calcium flux thereby maintaining glucose homeostasis.

BACKGROUND OF THE INVENTION

Several publications are referenced in this application by numbers in parentheses in order to more fully describe the state of the art to which this invention pertains. The disclosure of each of these publications is incorporated by reference herein.

Silent information regulator 2 (Sir2) proteins (also referred to as sirtuins) are well conserved across all kingdoms of life and are implicated in the control of gene silencing, apoptosis, metabolism, and aging (1-6). Sir2 is required for life-span increases in yeast, flies and Nvorms caused by caloric restriction or by natural antioxidants (e.g. resveratrol) (7, 8). Among the seven mammalian Sir2 homologs, SIRT1/Sir2alpha regulates skeletal muscle differentiation (9), represses damage-responsive Forkhead transcription factors (3, 4), negatively controls p53 to promote cell survival under stress (reviewed in (10)), and promotes fat mobilization in white adipocytes (11). Human SIRT2 is associated with microtubules in the cytoplasm and can deacetylate alpha-tubulin (12). Though the role of mitochrondrial SIRT3 is unknown (13, 14), variability of the human SIRT3 gene is associated with survivorship in the elderly (15).

Sir2 proteins catalyze a unique protein deacetylation reaction that requires the co-enzyme $NAD^+$, a key intermediate in energy metabolism. In this reaction, nicotinamide (vitamin B3) is liberated from $NAD^+$ and the acetyl-group of substrate is transferred to cleaved $NAD^+$, generating a novel metabolite O-acetyl-ADP ribose, OAADPr (16-20). Although genetic studies have linked Sir2 to diverse phenotypes, few reports have investigated the biological function(s) of OAADPr and its possible connection with the observed Sir2-dependent biology. It has been suggested that OAADPr might be a substrate for other linked enzymatic processes, an allosteric regulator, or a second messenger. The first report of bioactivity came from the observation that OAADPr injected into starfish oocytes or blastomeres caused a block/delay in maturation and cell division, respectively (21). Enzymes capable of metabolizing OAADPr have been detected in several diverse cells (22). In vitro, select members of the ADP-ribose hydrolase (Nudix) family of enzymes (e.g., mNudT5 and yeast YSA1) are capable of efficient hydrolysis of OAADPr, while others like human Nudt9 are not (22). Interestingly, the long transient receptor potential channel 2 (TRPM2) has been shown to contain a C-terminal Nudix box (23). This Nudix motif is proposed to bind ADP-ribose, stimulating the $Ca^{2+}$ channel activity of TRPM2 by initiating conformational changes leading to the opening of the channel pore (23-25). These findings prompted us to examine whether the TRPM2 ADP ribose gated $Ca^{2+}$ channel could be activated/regulated by OAADPr.

SUMMARY OF THE INVENTION

In accordance with the present invention, materials and methods are provided for modulating calcium flux, glucose homeostasis and apoptosis.

In one embodiment, a method for modulating glucose homeostasis in a patient in need thereof is provided. An exemplary method entails contacting an islet cell with an effective amount of an agent that increases intracellular levels of 0-acetyl-ADP-ribose or inhibits the breakdown thereof, the increase O-acetyl ADP ribose concentration resulting in cellular depolarization and/or Ca2+ entry which modulates insulin secretion from said cell. An agent suitable for use in the method comprises puromycin. Alternatively, the agent may be a functional analog of 0-acetyl-ADP-ribose. In an alternative embodiment, the method further comprises administration of an agent which inhibits sirtuin activity thereby preventing islet cell death in the patient. Exemplary agents for this purpose comprise nicotinamide.

In yet another embodiment of the invention, a composition comprising nicotinamide for inhibiting beta cell apoptosis induced by elevated levels of O-acetyl-ADP-ribose is provided. Additionally, a composition for modulating O-acetyl-ADP-ribose levels in a cell is disclosed. An exemplary composition for this purpose comprises puromycin and nicotinamide in a pharmaceutically acceptable carrier.

Another embodiment of the invention entails a method for modulating cell death in a target cell. An exemplary method entails contacting a cell comprising 0-acetyl-ADP-ribose and the long transient receptor potential channel 2 (TRPM2) with an agent which inhibits breakdown or increases intracellular concentrations of said 0-acetyl-ADP-ribose to levels sufficient to induce cell death in said target cell. It has been discovered in accordance with the present invention that the increase in the intracellular concentration of 0-acetyl-ADP-ribose induces persistent opening of the long transient receptor potential channel 2 (TRPM2) and thereby disrupts intracellular calcium homeostasis and inducing cell death in the target cell. The method optionally comprises contacting the cell with a second agent suspected of modulating TRPM2 activity, and assessing the effect of said agent on a said activity. Activities that may be assessed in accordance with the invention include, without limitation, modulation of cell death induced by puromycin administration, ion transport, conductivity of plasma membrane, and intracellular calcium mobilization and insulin secretion. The method may also entail contacting the cell with a second agent suspected of modulating TRPM2 channel activity and assessing the effect of said second agent on sirtuin-dependent cell death, the second agent optionally being nicotinamide.

Also encompassed within the present invention are siRNA molecules which are effective to downregulate sirtuin mRNA production.

In yet another aspect, a method for identifying agents which regulate TRPM2 channel opening is provided. An exemplary method comprises contacting a cell with an agent which modulates intracellular concentration of 0-acetyl-ADP-ribose and determining the effect of said agent on said channel opening as a function of ion flux into said cell, agents which alter said ion flux being effective to gate the TRPM2 channel. In a preferred embodiment, the cell to be contacted is a beta islet cell and the method further comprises determining the effect of the agent on insulin secretion. Optionally, the cell is present in an animal and the method further comprises determining the effect of the agent on glucose homeostasis in the animal.

BRIEF DESCRIPTION OF THE DRAWINGS

FIG. 1d.) Cytoplasmic OAADPr esterase activity is inhibited by puromycin. 200 µM O-[$^3$H]AADPr and 0-100 µM puromycin were added to cytoplasmic HEK-293 extract for 30 min. Percent hydrolysis of O-[$^3$H]AADPr to [$^3$H]acetate was measured as described hereinbelow. FIG. 1e.) Nuclear OAADPr acetyltransferase activity is not inhibited by puromycin. HEK-293 nuclear extract was incubated with 200 µM O-[$^3$H]AADPr in the presence or absence of 100 µM puromycin for 60 min. The reactions were quenched and resolved by HPLC. The radioactivity in collected fractions was determined by liquid scintillation counting. FIGS. 1f-g.) In vivo detection of OAADPr. Mass spectrum of HEK-293 generated OAADPr (peak m/z of 602.0894; the theoretical m/z for OAADPr is 602.0895) after puromycin treatment, with authentic [$^{13}$C]-OAADPr (peak m/z of 603.0851 and isotopic distribution of 604.0878 and 605.0928) as a standard. Peak 599.3691 is from the matrix. FIG. 1g shows two control data sets (no puromycin added), where the 602 peak is not distinguishable above the background.

FIG. 3. a.) Nicotinamide blocks puromycin induced cell death in TRPM2 expressing cells. TRPM2-expressing HEK-293 cells were exposed to 0-50 µM puromycin for 16 h in the presence (open diamond) or absence (closed diamond) of 500 µM nicotinamide. Cell survival was determined by measuring fluorescence of calcein in live cells. b.) PARP inhibitor 3-amino-benzamide does not block puromycin induced cell death. TRPM2-expressing HEK-293 cells were exposed to 0-50 µM puromycin for 16 h in the presence (open diamond) or absence (closed diamond) of 1.5 mM 3-aminobenzamide. Cell survival was determined as described in (a). Results (with standard deviations) are representative of two or more independent experiments.

FIG. 4 a) OAADPr gates the endogenous TRPM2 channel in CRI-G1 cells. Left panel: Evolution of currents in CRI-G1 cells in the absence (grey squares) or presence (black circles) of OAADPr (120-250 µM). Shown are average leak subtracted currents from n=3 cells for each condition. Right panel: Representative leak subtracted whole cell I/V curves for peak currents observed in the absence (grey line) and presence (black line) of OAADPr. For the above measurements, CRI-G1 cells were maintained in the whole cell patch clamp configuration as previously described for HEK-293 cells (44). b) Puromycin leads to cell death in CRI-G1 cells. CRI-G1 cells were treated with 0-40 µM puromycin for 16 h. Cell viability was assessed by measuring fluorescence of calcein in live cells. Data obtained from 4 independent experiments were plotted as a percent change in fluorescence compared to those of untreated cells set at a 100%. Error bars indicate the standard deviation from the mean. (Inset) Nicotinamide rescues puromycin-induced death in CRI-G1 cells. CRI-G1 monolayers were treated with 0, 0.5, 2, 4, 10 or 20 mM nicotinamide. After 30 minutes, puromycin was added to the media at a final concentration of 20 µM. Cell viability was assessed 16 h later as described above. Data are representative of two independent experiments performed in duplicate.

DETAILED DESCRIPTION OF THE INVENTION

Figure 1:
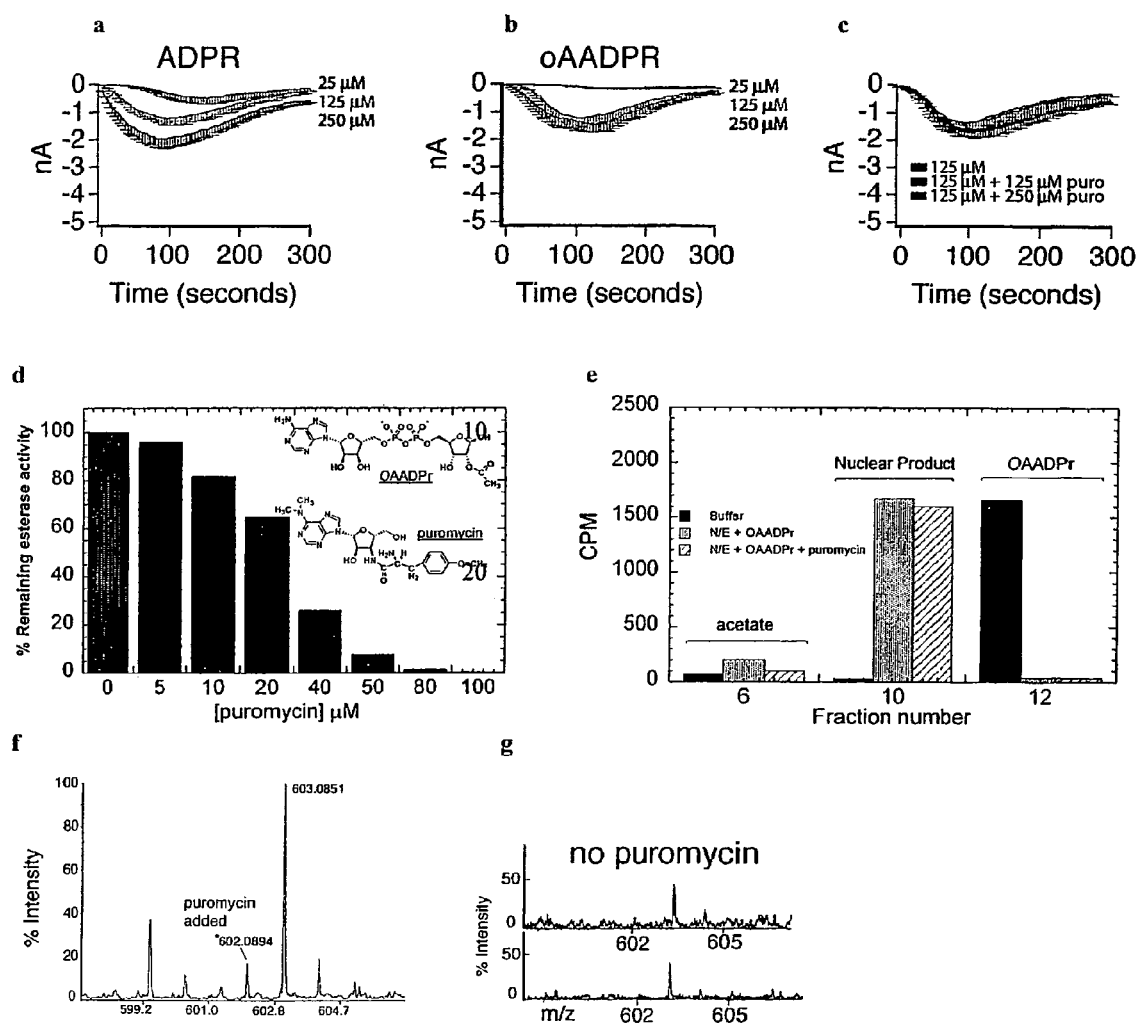
FIGS. 1. a-c demonstrate that the TRPM2 channel is gated by OAADPr in tet-induced HEK-293 cells. Shown is the development of whole cell currents over time in TRPM2-expressing HEK-293 cells. Bath solution was standard ringer's, and pipette solution was Cs-based and included 10 mM EGTA to buffer intracellular $Ca^{2+}$ to 10 nM. The patch pipette contained various concentrations of (FIG. 1a) ADPr, (FIG. 1b) OAADPr (FIG. 1c) OAADPr and puromycin as indicated in the figure.

Nonselective cation channels, like TRPM2, play a role in insulin secretion by regulating pancreatic beta-cell plasma membrane potential, Ca(2+) homeostasis, and thus glucose signaling and homeostasis (Qian F, Huang P, Ma L, Kuznetsov A, Tamarina N, Philipson L H. TRP genes: candidates for nonselective cation channels and store-operated channels in insulin-secreting cells. Diabetes. 2002 February; 51 Suppl 1:S183-9.) TRPM2 is expressed in human islets. As described herein, TRPM2 is activated by OAADPr in an insulinoma cell line. TRPC-like channels and their activation by OAADPr-producing Sirtuin enzymes provide a mechanism for depolarization or Ca(2+) entry in beta-cells (insulin producing cells), which in turn modulates control of insulin secretion and overall glucose homeostasis. Thus, in one aspect the invention provides materials and methods for modulating glucose homeostasis.

In yet another aspect, it has been discovered that elevation in O-acetyl-ADP ribose to toxic levels triggers apoptotic cell death. The methods described herein are useful for inducing cell death in targeted cell types and should have therapeutic value in treating disorders associated with aberrant cell proliferation, such as cancer. Target cells for use in the disclosed methods include, without limitation, cancer cells, virally infected cells, B cells, T cells and macrophages. Targeting immune cells for programmed cell death can have therapeutic value in the treatment of Alzheimer's disease, for example.

Silent information regulator 2 (Sir2) proteins or sirtuins are histone/protein deacetylases that regulate gene silencing, apoptosis, metabolism, and aging. Sir2 proteins catalyze a unique protein deacetylation reaction that absolutely requires the co-enzyme $NAD^+$ and generates a novel metabolite O-acetyl-ADP ribose, OAADPr, whose function is unknown. Here we show that OAADPr directly activates the long transient receptor potential channel 2 (TRPM2), a $Ca^{2+}$ permeable nonselective ion channel. TRPM2 channel over-stimulation by inhibiting the cellular breakdown of OAADPr leads to cell death, which is attenuated by a loss in endogenous levels of Sir2 homologues, SIRT2 and SIRT3. These data provide the further evidence for the existence of cellular OAADPr and its potential role in controlling the TRPM2 channel, whose activity is known to confer susceptibility to cell death by oxidative stress and diabetogenic agents. Notably, agents such as nicotinamide can be used effectively to reduce intracellular O-acetyl-ADP ribose levels. Nicotinamide or niacinamide is commercially available from Arco Pharmaceuticals Inc, Bohemia N.Y. and from Sirius Laboratories Inc. Vernon Hills, Ill. Thus, methods for preventing of the onset of Type I Diabetes by use of nicotinamide or other inhibitors of sirtuin (e.g., Sir SiRNAs) are also encompassed in the present invention. Such methods effectively lower the production of 0-acetyl-ADP ribose which in turn lowers activation of the TRPM2 channel thereby preventing beta-islet cell death. On the other hand, if insufficient insulin production is due to abnormally low TRPM2 activity in beta cells, then agents which increase the intracellular concentration of O-acetyl-ADP-ribose (i.e., prevent breakdown of endogenous O-acetyl-ADP-ribose or use of O-acetyl-ADP-ribose analogues acting as agonists or administration of purinomycin) would be useful for modulating insulin secretion by these cells and maintaining proper blood glucose levels.

The following materials and methods are provided to facilitate the practice of the present invention.

Channel Gating.

Patch clamp electrophysiology was performed as previously described (23). Briefly, cells were patch clamped in the whole cell configuration at 25° C. using pipettes with resistances ranging from 2-3 MOhms. Currents were recorded on an EPC9 patch clamp amplifier with automatic capacitance compensation using a protocol generating a 50 msec voltage ramp from −100 to +100 mv every two seconds at a holding potential of 0 mv (appropriately corrected for liquid junction potential). Bath solution included 150 mM NaCl, 2.8 mM KCl, 5 mM CsCl, 1 mM $CaCl_2$, 2 mM $MgCl_2$, and 10 mM Hepes (pH 7.2). Pipette solution included 135 mM CsGlutamate, 1 mM $MgCl_2$, 8 mM NaCl, 10 mM Hepes (pH 7.2), and 10 mM EGTA. For low-resolution presentation of current development over the course of the experiment, instantaneous currents at −80 mv were extracted from each ramp and plotted versus time.

Cell Culture.

HEK-293 and tetracycline (tet)-inducible HEK-293 TRPM2-expressing cells (23) were cultured in DMEM and 10% FBS at 37° C., 5% $CO_2$. Media used to culture tet-inducible HEK-293 cells was supplemented with blasticidin (5 μg ml$^{-1}$; Invitrogen) and zeocin (0.4 mg/ml; Invitrogen). To induce expression of TRPM2 in recombinant HEK-293 cells, tetracycline was added to the media at 1 μg ml$^{-1}$ (Invitrogen) 24 h prior to experiments. The CRI-G1 rat β-islet tumor cell line was obtained from EACC and cultured in DMEM, 10% FBS and 2 mM glutamine.

Synthesis and Purification of O-[$^3$H]AADPr.

As previously described (16, 19, 22, 26), O-[$^3$H]AADPr was generated in a reaction including 50 mM Tris, 7.5, 1 mM DTT, 1 mM [$^3$H]-acetylated histone peptide, 700 μM $NAD^+$, and Sir2 enzyme. After 60 min, NADase was added to degrade the remaining $NAD^+$. The reaction was quenched in 1% TFA and O-[$^3$H]AADPr was separated from other components in the reaction by reversed phase HPLC (16, 19, 22, 26). Based on HPLC, MS and NMR analyses, the OAADPr is >95% pure.

Conversion Assays with OAADPr.

Cytoplasmic and nuclear extracts were prepared from HEK-293 cells as previously described (22). To detect esterase activity (22), cytoplasmic extract was incubated with 200 μM O-[$^3$H]AADPr in the presence of 0-100 μM puromycin for 30 min. Activated charcoal slurry in PBS, pH 7.0 was added to quench the reaction and bind O-[$^3$H]AADPr. Samples were vortexed and centrifuged. Aliquots of the supernatant containing [$^3$H]acetate were removed and analyzed by liquid scintillation counting. To detect nuclear OAADPr metabolizing activity (22), nuclear extract was incubated with 200 μM O-[$^3$H]AADPr in the presence or absence of 100 μM puromycin for 60 min. The reaction was terminated by addition of TFA to 1%. Samples were injected onto a Beckman Biosys 510 HPLC system and a Vydac C18 (1.0 Å~25 mm) small pore preparative column (Vydac, Hesperia, Calif.) as previously described (22). Radioactivity in each elution fraction was measured by liquid scintillation counting.

Cell Viability Assays.

HEK-293, tet-inducible HEK-293, and CRI-G1 cells were seeded into 6 well plates at a density of 500,000 cells per well. When cells were 50-70% confluent, puromycin was added to the media at various concentrations for 16 hours. Cell monolayers were rinsed with PBS, after which 0.5 ml of 2 μM calcein in PBS was added directly to the well for 10-20 minutes. Calcein is retained in living, but not dead cells, where it undergoes catalytic conversion into a fluorescent compound Fluorescence in each well was measured in a microplate reader using excitation and emission filters at 485/530 nm, respectively.

Matrix-Assisted Laser Desorption Ionization Mass Spectrometry Analyses.

MALDI mass spectrometry was performed at the Environmental Health Sciences Center, Oregon State University as described previously (16). Cell monolayers were washed with PBS, pH 7.4 and scraped off the culture dish. Cells were sedimented, rinsed with PBS, and sedimented again at 16,000×g for 20 s at 4° C. The pellet was resuspended in 0.05% TFA/$H_2O$. The suspension was vortexed, and incubated on ice, interspersed by 5 quick bursts of sonication. Cellular debris was removed by centrifugation, and the supernatant stored at −20° C., prior to reverse phase HPLC analysis.

Knockdown of SIRT2 and SIRT3 Transcription Using siRNA.

Tet-inducible HEK-293 cells were transfected with 100 nM control, SIRT2 or SIRT3 siRNA (Dharmacon) using Trans-IT TKO transfection reagent (Mirus). After 24 hours, TRPM2 expression was induced by adding tetracycline to the media. 48 hours post transfection, one set of cells was harvested and analyzed for SIRT expression as described below, and the rest were treated with puromycin for an additional 16 h and assayed for viability.

Analysis of SIRT2 and SIRT3 Transcripts by RT-PCR.

Total RNA was isolated from harvested cells using TRIzol Reagent (Invitrogen). RNA was reverse transcribed using random hexamers and AMV-RT (Promega). The RT reaction was used as a template for PCR amplification of SIRT2 or SIRT3 using primer pairs: 5'CAGAACATAGATAC CCTG-GAGCGAA (SEQ ID NO: 1) and 5'AAGGTCCTC-CAGCTCCTTCTTC (SEQ ID NO: 2); and 5'TGAGAGAGT-GTCGGGC ATCCCTG (SEQ ID NO: 3) and 5'TCATCCTATTTGTCTGGTCCATCAA (SEQ ID NO: 4), respectively. Primers 5'GGCACCA CACCTTATACAAT (SEQ ID NO: 5) and 5'ATGTCACGCACGATTTCC (SEQ ID NO: 6) were used to amplify actin which served as an internal PCR control.

Detection of SIRT2 and SIRT3 Protein by Western Blot Analysis.

Cells were lysed in 50 mM Tris-HCl pH 8.0, 150 mM sodium chloride, 1% Igepal CA-630, 0.5% sodium deoxycholate, 0.1% sodium dodecyl sulfate, 1 mM PMSF, 10 g/ml aprotinin and 10 ug/ml leupeptin. Cytosolic and mitochondrial fractions were separated using a mito-chondrial isolation kit (Pierce) according to manufacturer's instructions. SIRT2 and SIRT3 protein was detected by standard Western blot protocol using chicken anti SIRT2 antibody (12) and rabbit anti SIRT3 antisera (14) respectively (Antibodies were graciously provided by Dr. Eric Verdin, UCSF).

The following example is provided to illustrate an embodiment of the invention. It is not intended to limit the invention in any way.

Example 1

To test whether OAADPr could indeed regulate the TRPM2 channel, electrophysiology studies were performed in TRPM2-expressing HEK-293 cells. We found that inclusion of OAADPr in the patch pipette solution induces TRPM2 gating with similar kinetics and dose dependence to that of ADP-ribose in whole cell recordings (FIGS. 1a and 1b). It is important to note that OAADPr exists in an ~50:50 equilibrium between 2'-OAADPr and 3'-OAADPr (18, 19). If TRPM2 exhibits regio-selective binding for just one of the OAADPr forms, then the dosage-dependence for that form would be twice as potent as that observed in FIG. 1. The spontaneous breakdown of OAADPr to ADPr in the patch pipette was <5-10% in multiple experiments. These results provide initial evidence that OAADPr is capable of acting as a physiological regulator of TRPM2.

Figure 2:
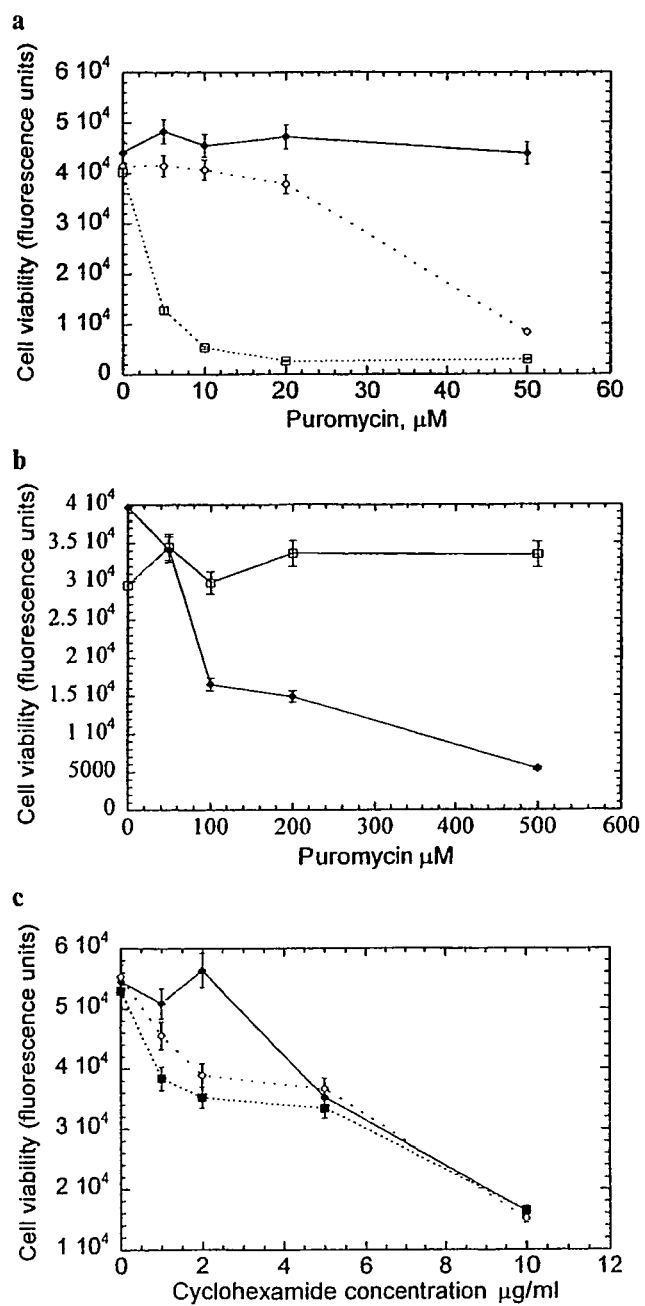
FIGS. 2 a-c demonstrate that puromycin leads to cell death in TRPM2-expressing HEK-293 cells. Shown are HEK-293 cells (closed diamond) and HEK-293 cells stably transfected with a tet-controlled TRPM2 construct in the presence (open squares) or absence of (open diamonds) tetracycline. Cells incubated in the presence of 0-50 µM puromycin for 16 h were assayed for viability by measuring fluorescence of calcein in live cells. b.) Removal of calcium rescues cells from puromycin induced cell death. TRPM2-expressing HEK-293 cells were grown in complete DMEM media and 1 µg/ml tetracycline until 80-90% confluent. One set of cells were re-fed with the same complete media (closed diamonds) and the other set of cells were rinsed with PBS and fed with modified media containing 1 µg/ml tetracycline, 5 mM EGTA and without calcium chloride (open squares). One hour after calcium removal, cells were incubated in 0-500 µM puromycin for 6 hours after which cell viability was measured. c.) TRPM2 expression in HEK-293 cells does not lead to preferential sensitivity to cycloheximide. HEK-293 (close diamond) and TRPM2 expressing HEK-293 cells in the absence (open diamond) or presence of (closed square) tetracycline were exposed to 0-10 µg/ml cycloheximide for 16 h. Cell viability was determined as described in (a).

In an effort to identify pharmacological compounds that could inhibit the breakdown of cellular OAADPr and provide a physiological link between channel activity and OAADPr levels, we searched for compounds structurally similar to OAADPr. We identified (FIG. 1d) the anti-tumor antibiotic puromycin (27, 28). In mammalian cells, at least two major OAADPr metabolizing activities have been reported, a cytosolic esterase and a nuclear acetyltransferase (22). Using these previously described OAADPr-consuming activity assays (22), we found that puromycin was a potent inhibitor of the OAADPr esterase, but not of the nuclear acetyltransferase activity (FIGS. 1d and 1e). As shown in FIG. 2d, puromycin could substantially inhibit the cytosolic esterase activity in HEK-293 cells at 5 µM puromycin. By 80 µM the esterase activity was completely inhibited by puromycin. In contrast, 100 µM puromycin had no effect on the nuclear OAADPr-metabolizing activity in HEK-293 cells (FIG. 1e), demonstrating the specificity of puromycin toward the OAADPr esterase. By inhibiting the cytoplasmic breakdown of OAADPr, puromycin provided a pharmalogical tool to elevate OAADPr levels and examine its effect on TRPM2 channel activity. Sir2 homologs are expressed in HEK-293 cells, as protein extracts display $NAD^+$-dependent histone deacetylase activity that is inhibited by nicotinamide (data not shown). To demonstrate that puromycin could increase the cellular levels of OAADPr, HEK-293 cells either treated or mock-treated with puromycin were analyzed for the presence of OAADPr, using HPLC fractionation and mass spectrometry. Detection of OAADPr in mock-treated cells was negligible, whereas puromycin-treated cells displayed significantly detectable levels of OAADPr (FIGS. 1f and 1g). Although direct quantitation was not possible, these results provide the first evidence that OAADPr is produced in cells.

Next, using an inducible tetracycline (tet) expression system for TRPM2 stably transfected HEK-293 cells (23), we examined whether puromycin could activate the channel through the accumulation of OAADPr. To verify that puromycin did not directly gate the TRPM2 channel, whole cell channel recordings were performed with 100 µM puromycin alone, which showed no affect on channel activity (data not shown). Also, there was no significant enhancement of OAADPr gated TRPM2 channel activity in whole cell recordings when 125-250 µM puromycin was included in the patch pipette (FIG. 1c). In addition to demonstrating that puromycin does not directly gate TRPM2, this result further supports the contention that OAADPr, and not the breakdown product ADPr, is the direct ligand in the recordings obtained in the absence of puromycin (FIG. 1b).

We predicted that if the TRPM2 channel exhibited sustained activation in HEK-293 cells treated with puromycin, then the influx of $Na^+$ and $Ca^{2+}$ should result in cell death through the loss of ionic homeostasis. To examine this prediction, we performed a series of cell survival studies with the TRPM2 stably transfected HEK-293 cells following puromycin treatment. Parental HEK-293 cells showed no significant cell death following puromycin treatment (5-50 µM) (FIG. 2a). In contrast, HEK-293 cells harboring the TRPM2 channel from tet-induced expression displayed a profound sensitivity to cell death with as little as 5 µM puromycin (FIG. 2a), following a strong dose-dependence up to 50 µM puromycin. When TRPM2 expression was not induced by tet, the cells exhibited nearly complete protection against puromycin-dependent cell death. Some cell death was observed at the highest puromycin level (50 µM), attributable to some leaky expression of the TRPM2 construct. Full activation of the TRPM2 channel was shown previously to be $Ca^{2+}$ dependent (29-31). To directly show that the observed cell death through TRPM2 was dependent on $Ca^{2+}$, puromycin induced cell death was assessed in $Ca^{2+}$-free media. The removal of $Ca^{2+}$ before puromycin treatment completely blocked puromycin-induced cell death in TRPM2 expressing cells (FIG. 2b). These results demonstrate that TRPM2 and $Ca^{2+}$ are critical for puromycin-dependent cell death in our inducible TRPM2 expression HEK-293 system.

Because puromycin is known to also inhibit protein translation, we examined whether inhibition of protein synthesis is responsible for the TRPM2-dependent cell death, perhaps through the loss of a protein involved in negatively regulating the channel. We tested whether cycloheximide, a strong inhibitor of translation, had the same effect as puromycin. As displayed in FIG. 2c, cells expressing TRPM2 exhibited no significant increased sensitivity to cycloheximide compared to the same cells that did not over-express the channel. Parental HEK-293 cells showed a similar dose-dependence of cell death to cycloheximide treatment (FIG. 2c). These data suggest that channel activation following puromycin treatment is not due to inhibition of translation, but rather, that puromycin leads to an accumulation of OAADPr levels, which can activate the TRPM2 channel.

Human cells contain the genes for at least 7 Sir2 homologs (32). To evaluate a link between Sir2 activity and TRPM2, we sought an approach that could down-regulate the activity of all Sir2-like proteins. Nicotinamide (B3 vitamin) is a potent inhibitor of Sir2 homologues (14, 33, 34). The inhibition results from trapping an enzyme intermediate, a common step in the mechanism of all Sir2 enzymes (35, 36). In yeast, nicotinamide treatment or genetic manipulation of endogenous nicotinamide levels were shown to directly affect Sir2 function (37). We investigated whether nicotinamide could protect TRPM2 expressing cells from puromycin-induced cell death, by preventing the production of OAADPr from endogenous Sir2 proteins. Indeed, nicotinamide (500 µM) could completely protect puromycin-induced cell death up to concentrations as high as 20 µM puromycin (FIG. 3a). Only at much higher puromycin (50 µM) could the protection afforded by nicotinamide be suppressed. These results suggest that the gating of the TRPM2 channel by OAADPr is a Sir2-dependent event. Although nicotinamide is also reported to inhibit PARP (38), the PARP inhibitor 3-aminobenzamide had no effect on the puromycin-induced cell death (FIG. 3b).

Next, we sought to substantiate our observations of OAADPr-gated TRPM2 activity using the genetically unmodified cell line, CRI-G1. CRI-G1 cells are a rat beta-islet tumor cell line (insulinoma), where the endogenous TRPM2 channel has been well-characterized (29, 30, 39, 40). As shown in FIG. 4a (left and right panels), inclusion of OAADPr in the patch pipette induced evolution of average currents of c.a. 2 nA with a highly linear I/V relationship characteristic of TRPM2. Importantly, essentially no current evolution occurred in the absence of OAADPr, and the evolution of the OAADPr-induced currents occurred over a time course consistent with diffusional equilibration of OAADPr into the cell from the patch pipette. Overall, these results are most simply interpreted as due to direct OAADPr-mediated gating of endogenous TRPM2 channels in CRI-G1 cells. Supporting the physiologic relevance of OAADPr in inducing TRPM2 gating, puromycin treatment of CRI-G1 cells lead to their dose-dependent death which could be blocked by the Sir2 inhibitor nicotinamide (FIG. 4B).

Figure 5:
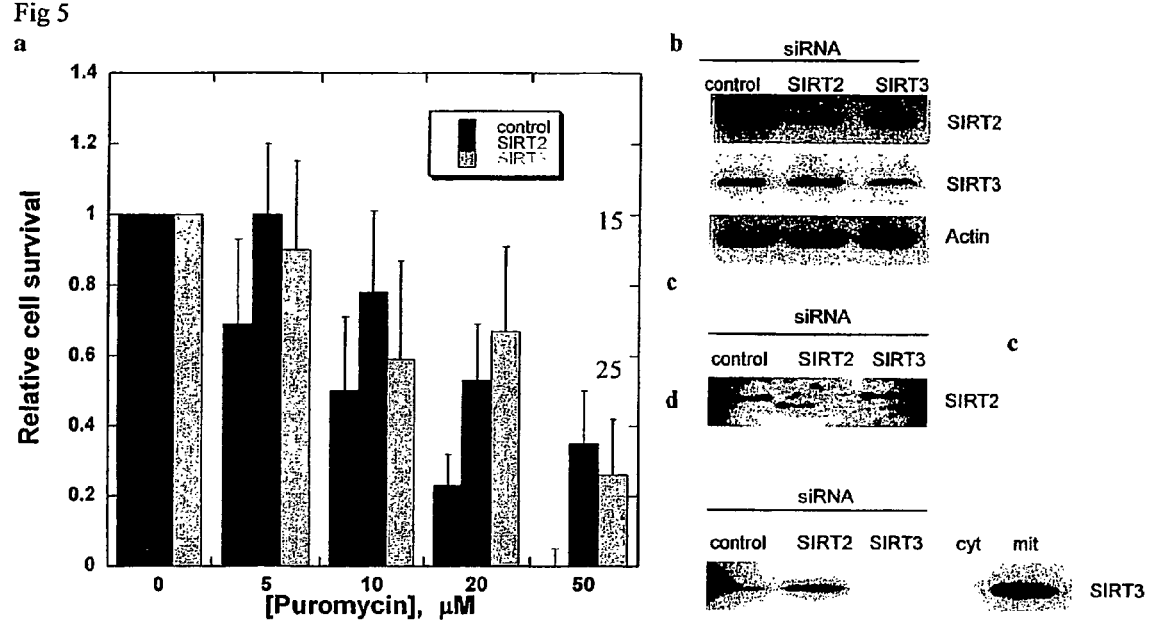
FIG. 5. a.) SiRNA knock down of endogenous SIRT2 and SIRT3 protein protects cells against puromycin-induced death. TRPM2-expressing HEK-293 cells were transfected with 100 nM nonspecific control, SIRT2 or SIRT3 siRNA. After 48 h, cells were exposed to 0-50 µM puromycin for an additional 16 h. Cell survival was determined by measuring fluorescence of calcein in live cells, and plotted as a percent relative to the nonspecific siRNA control. Results are averages (with standard deviations) from 5 separate experiments. b-d). Detection of SIRT2 and SIRT3 expression in siRNA treated TRPM2-expressing HEK-293 cells. Cells treated for 48 h with 100 nM control, SIRT2 or SIRT3 siRNA were harvested and analyzed for knock down in SIRT2 and SIRT3 expression. (b) The presence of SIRT2 and SIRT3 transcripts was detected by RT-PCR. The amount of total RNA used for RT-PCR was normalized to that of actin. (c) Endogenous SIRT2 protein levels were detected by Western blot using anti SIRT2 antibody. (d) SIRT3 protein, detected by Western blot using anti SIRT3 antisera, was detected in the mitochondrial but not the cytosolic fraction.

To identify which Sir2 enzymes were involved in production of OAADPr mediating puromycin-induced TRPM2 channel gating, we examined whether two likely candidates, cytoplasmic SIRT2 and mitochondrial SIRT3, were involved. The basis for choosing SIRT3 comes from a recent report indicating that mitochondria are a source of cytoplasmic ADPr, which activates the TRPM2 channel in response to oxidative stress (41). Although the enzymatic source of the ADPr or OAADPr was not addressed in that study, these observations give credence to the possibility that mitochondrial SIRT3 could generate OAADPr to activate the TRPM2 channel. RNA interference (siRNA) was used to knockdown the endogenous messenger RNA and protein levels, and the resulting effect on puromycin-induced cell death was assessed. In these experiments, a nonspecific siRNA control and siRNAs specific for SIRT2 and SIRT3 were used (FIG. 5). Each siRNA demonstrated strict specificity, only knocking down its corresponding RNA and protein, while having no effect on the other (FIG. 5). After siRNA treatment, endogenous levels of SIRT3 protein in whole cell extracts could no longer be detected. Similar knockdown was seen with SIRT2 siRNA treatment. Relative to non-specific siRNA transfection, cells transfected with either SIRT2 or SIRT3 siRNAs displayed significant resistance to puromycin-induced cell death in TRPM2 expressing HEK-293 cells (FIG. 5). The data presented in FIG. 5a are the averages of five separate experiments (including standard deviations) with five different concentrations of puromycin. At 20 µM puromycin, loss of SIRT2 or SIRT3 increased cell survival by 2-3 fold, and by 50 µM puromycin, ~30% of the original cell number had survived, whereas control siRNA-treated cell survival was negligible (FIG. 5A). These results suggest that both SIRT2 and SIRT3 may contribute to the accumulation of cellular OAADPr, leading to TRPM2-dependent cell death.

The TRPM2 $Ca^{2+}$-permeable channel can be activated by oxidative stress ($H_2O_2$) (25, 42, 43) and ADP-ribose (24, 25, 44), and confers susceptibility to cell death (42). TRPM2 is highly expressed in rat microglia (25), and has been described in neutrophil granulocytes, a monocytic cell line U937 (24, 44), rat insulinoma cell lines (39, 42) and pancreatic β-cells (45, 46). In whole rat studies, puromycin treatment leads to specific pancreatic cell death, an effect that was not the result of inhibition of protein synthesis (47). The molecular basis for this susceptibility was not known. In light of our data, it is likely that puromycin selectively targets TRPM2 expressing cells, causing an influx of $Na^{2+}/Ca^{2+}$ and subsequent cell death. Consistent with this idea and the involvement of Sir2 proteins, prophylactic treatment with nicotinamide has been shown to suppress the development of diabetes in several animal models by protecting insulin-producing β-cells from destruction by diabetogenic agents (alloxan and streptozotocin) that induce reactive oxygen species (48). The susceptibility of β-cells to alloxan and other oxidative insults has been linked to the overactivation of TRPM2 channels (39). Oxidative stress or other cellular insults like puromycin could trigger a stress response through several mechanisms that ultimately lead to activation of the TRPM2 channel. It is possible that both ADPr and OAADPr are physiologically important in regulating the channel, but are generated from diverse cellular stimuli and/or different pathways. Here we provide evidence suggesting that Sir2 enzymes may play an important role in mediating the cytotoxic effects of certain pharmacological agents. Furthermore, these results have an important impact on the use of puromycin for the treatment of cancer because of its potential destruction of cells expressing TRPM2, particularly insulin-producing cells.

An emerging picture of Sir2 function in diverse organisms is the regulation of responses to cellular stress that include protein oxidation (49), DNA damage (50), caloric restriction (51), among others (52). Here, we provide the first evidence that OAADPr, the product of the Sir2 reaction, can modulate cellular responses by regulating the opening of the TRPM2 $Ca^{2+}$-permeable channel. Although puromycin treatment and subsequent accumulation of OAADPr causes susceptibility to cell death, these data suggest that at lower levels of OAADPr, Sir2-like enzymes could modulate diverse cellular events by mediating cellular $Ca^{2+}$ entry. Nonselective cation channels, like TRPM2, appear to play a role in insulin secretion by regulating pancreatic beta-cell plasma membrane potential, $Ca^{2+}$ homeostasis, and thus glucose signaling and homeostasis (46). TRPM2 is expressed in human islets, and we have shown herein that TRPM2 is activated by OAADPr in an insulinoma cell line. TRPC-like channels and their activation by OAADPr-producing Sirtuin enzymes provide mechanism for depolarization or $Ca^{2+}$ entry in beta-cells (insulin producing cells), which could lead to the control of insulin secretion and overall glucose homeostasis. Consistent with our findings, the Sir2p homolog in the yeast K. lactis was shown to regulate either the intake or efflux of a subset of divalent metal cations, suggesting that Sir2p has a role in cation transport in that organism (53). The dichotomy of $Ca^{2+}$ as a survival factor and as mediator of apoptotic and necrotic cell death reflects the importance of tightly controlling the entry and the sub-cellular compartmentalization of calcium (54). OAADPr adds to the list of NAD+-derived second messengers (including ADPr, cyclic-ADPr and NAAD(P)) that regulate $Ca^{2+}$ signaling/release (55).

REFERENCES

1. D. Moazed, *Curr. opin. Cell Biol.* 13, 232-238 (2001).
2. S. M. Gasser, M. M. Cockell, *Gene* 279, 1-16 (Nov. 14, 2001).
3. A. Brunet et al., *Science* (Feb. 19, 2004).
4. M. C. Motta et al., *Cell* 116, 551-63 (Feb. 20, 2004).
5. V. J. Starai, H. Takahashi, J. D. Boeke, J. C. Escalante-Semerena, *Curr Opin Micirobiol* 7, 115-9 (April 2004).
6. S. Hekimi, L. Guarente, *Science* 299, 1351-4 (Feb. 28, 2003).
7. K. T. Howitz et al., *Nature* 425, 191-6 (Sep. 11, 2003).
8. J. G. Wood et al., *Nature* in press (2004).
9. M. Fulco et al., *Mol Cell* 12, 51-62 (July 2003).
10. J. Smith, *Trends Cell Biol* 12, 404-6 (September 2002).
11. F. Picard et al., *Nature* 429, 771-6 (Jun. 17, 2004).
12. B. J. North, B. L. Marshall, M. T. Borra, J. M. Denu, E. Verdin, *Mol Cel* 11, 437-44 (February 2003).
13. P. Onyango, I. Celic, J. M. McCaffery, J. D. Boeke, A. P. Feinberg, *Proc Natl Acad Sci USA* 99, 13653-8 (Oct. 15, 2002).
14. B. Schwer, B. J. North, R. A. Frye, M. On, E. Verdin, *J Cell Biol* 158, 647-57 (Aug. 19, 2002).
15. G. Rose et al., *Exp Gerontol* 38, 1065-70 (October 2003).
16. K. G. Tanner, J. Landry, R. Sternglanz, J. M. Denu, *Proc Natl Acad Sci USA*. 97, 14178-82 (2000).
17. J. C. Tanny, D. Moazed, *Proc. Natl. Acad Sci. USA* 98, 415-420 (2001).
18. A. A. Sauve et al., *Biochemistry* 40, 15456-15463 (2001).
19. M. D. Jackson, J. M. Denu, *The Journal of Biological Chemistry* 277, 18535-18544 (2002).
20. J. M. Denu, *TIBS* 28, 41-48 (2003).
21. M. T. Borra et al., *J Biol Chem* 277, 12632-41 (Apr. 12, 2002).
22. L. A. Rafty, M. T. Schmidt, A.-L. Perraud, A. M. Scharenberg, J. M. Denu, *Journal of Biological Chemistry* 277, 47114-47122 (2002).
23. A.-L. Perraud et al., *Nature* 411, 595-599 (2001).
24. Y. Sano et al., *Science* 293, 1327-30 (Aug. 17, 2001).
25. R. Kraft et al., *Am J Physiol Cell Physiol* 286, C129-37 (January 2004).
26. M. T. Borra, J. M. Denu, *Methods Enzymol* 376, 171-87 (2004).
27. A. B. Pardee, R. Dubrow, *Cancer* 39, 2747-54 (June 1977).
28. R. Schlapbach, A. Fontana, *Biochim Biophys Acta* 1359, 174-80 (Nov. 27,1997).
29. P. S. Herson, M. L. Ashford, *J Physiol* 514 (Pt 1), 47-57 (Jan. 1, 1999).
30. P. S. Herson, K. Lee, R. D. Pinnock, J. Hughes, M. L. Ashford, *J Biol Chem* 274, 833-41 (Jan. 8, 1999).
31. D. McHugh, R. Flemming, S. Z. Xu, A. L. Perraud, D. J. Beech, *J Biol Chem* 278, 11002-6 (Mar. 28, 2003).
32. R. A. Frye, *Biochem. Biophys. Res. Commun.* 273, 793-798 (2000).
33. K. J. Bitterman, R. M. Anderson, H. Y. Cohen, M. Latorre-Esteves, D. A. Sinclair, *Journal of Biological Chemistry* 277, 45099-107 (2002).
34. J. Landry, J. T. Slama, R. Sternglanz, *Biochem. Biophys. Res. Commun.* 30, 685-690 (2000).
35. M. D. Jackson, M. T. Schmidt, N. J. Oppenheimer, J. M. Denu, *J Biol Chem* 278, 50985-98 (Dec. 19, 2003).
36. A. A. Sauve, V. L. Schramm, *Biochemistry* 42, 9249-56 (Aug. 12, 2003).
37. R. M. Anderson, K. J. Bitterman, J. G. Wood, O. Medvedik, D. A. Sinclair, *Nature* 423, 181-5 (May 8, 2003).
38. G. J. Southan, C. Szabo, *Curr Med Chem* 10, 321-40 (February 2003).
39. P. S. Herson, M. L. Ashford, *J Physiol* 501 (Pt 1), 59-66 (May 15, 1997).
40. K. Inamura et al., *J Membr Biol* 191, 201-7 (Feb. 1, 2003).
41. A. L. Perraud et al., *J Biol Chem* in press (2004).
42. Y. Hara et al., *Mol Cell* 9, 163-73 (January 2002).
43. E. Wehage et al., *J Biol Chem* 277, 23150-6 (Jun. 28, 2002).
44. A. L. Perraud et al., *Nature* 411, 595-9 (May 31, 2001).
45. P. Krippeit-Drews et al., *J Physiol* 514 (Pt 2), 471-81 (Jan. 15, 1999).
46. F. Qian et al., *Diabetes* 51 Suppl 1, S183-9 (February 2002).
47. D. S. Longnecker, *Lab Invest* 26, 459-64 (April 1972).
48. H. Kolb, V. Burkart, *Diabetes Care* 22 Suppl 2, B16-20 (March 1999).
49. H. Aguilaniu, L. Gustafsson, M. Rigoulet, T. Nystrom, *Science* 299, 1751-3 (Mar. 14, 2003).
50. J. Luo et al., *Cell* 107, 137-48 (Oct. 19, 2001).
51. S. J. Lin, P. A. Defossez, L. Guarente, *Science* 289, 2126-8 (Sep. 22, 2000).
52. M. Kaeberlein, A. A. Andalis, G. R. Fink, L. Guarente, *Mol Cell Biol* 22, 8056-66 (November 2002).
53. S. U. Astrom, A. Kegel, J. O. Sjostrand, J. Rine, *Genetics* 156, 81-91 (September 2000).
54. S. Orrenius, B. Zhivotovsky, P. Nicotera, *Nat Rev Mol Cell Biol* 4, 552-65 (July 2003).
55. F. Berger, M. H. Ramirez-Hernandez, M. Ziegler, *Trends Biochem Sci* 29, 111-8 (March 2004).
56. Elliott, R. B., Pilcher C C, Fergusson D M, Stewart A W. *J. Pediatr Endocrinology Metab.* 9:501-509 (September-October 1996).
57. Elliott R B, Chase H P *Diabetologia* 34:362-365 (May 1991).

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for modulating glucose homeostasis in a diabetic patient in need thereof comprising: contacting an islet cell with an effective amount of a first agent that increases intracellular levels of O-acetyl-ADP-ribose, said increase in concentration resulting in cellular depolarization and/or $Ca^{2+}$ entry which increases insulin secretion from said cell, wherein said first agent is O-acetyl-ADP-ribose, and contacting said islet cell with a second agent which inhibits sirtuin activity thereby preventing islet cell death in said patient, wherein said second agent is nicotinamide or a sirtuin siRNA.

2. The method of claim 1, wherein said second agent is nicotinamide.

3. The method of claim 1, wherein said second agent is a sirtuin siRNA.

* * * * *

UNITED STATES PATENT AND TRADEMARK OFFICE
CERTIFICATE OF CORRECTION

PATENT NO. : 8,440,638 B2  Page 1 of 1
APPLICATION NO. : 11/658069
DATED : May 14, 2013
INVENTOR(S) : Denu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1880 days.

Signed and Sealed this
Eighth Day of September, 2015

Michelle K. Lee
*Director of the United States Patent and Trademark Office*